(12) United States Patent
Diener et al.

(10) Patent No.: US 9,894,905 B2
(45) Date of Patent: Feb. 20, 2018

(54) MIXED CRYSTALS, METHOD FOR THE PRODUCTION THEREOF AND USE THEREOF IN THE PRODUCTION OF BAKED GOODS

(75) Inventors: Ralf Diener, Neustadt (DE); Jürgen Schneider, Bobenheim am Berg (DE); Herbert Seiter, Schindhard (DE); Manfred Schäfer, Limburgerhof (DE); Walther Schmid, Mannheim (DE)

(73) Assignee: BASF SE, Ludwigshafen (DE)

( * ) Notice: Subject to any disclaimer, the term of this patent is extended or adjusted under 35 U.S.C. 154(b) by 139 days.

(21) Appl. No.: 13/141,855

(22) PCT Filed: Dec. 16, 2009

(86) PCT No.: PCT/EP2009/067301
§ 371 (c)(1),
(2), (4) Date: Jun. 23, 2011

(87) PCT Pub. No.: WO2010/072637
PCT Pub. Date: Jul. 1, 2010

(65) Prior Publication Data
US 2011/0257272 A1    Oct. 20, 2011

(30) Foreign Application Priority Data
Dec. 23, 2008    (EP) .................... 08172799

(51) Int. Cl.
| | | |
|---|---|---|
| *A21D 2/18* | (2006.01) | |
| *A21D 10/00* | (2006.01) | |
| *A21D 2/14* | (2006.01) | |
| *A21D 2/36* | (2006.01) | |

(52) U.S. Cl.
CPC .......... *A21D 10/005* (2013.01); *A21D 2/145* (2013.01); *A21D 2/188* (2013.01); *A21D 2/36* (2013.01)

(58) Field of Classification Search
CPC .......... A21D 2/145; A21D 2/36; A21D 2/188; A21D 2/04; A21D 10/005
See application file for complete search history.

(56) References Cited

U.S. PATENT DOCUMENTS

| | | | |
|---|---|---|---|
| 1,643,951 A | 10/1927 | Leo | |
| 2,791,508 A | 5/1957 | Rivoche | |
| 3,170,796 A * | 2/1965 | Andre et al. | 426/554 |
| 3,388,990 A | 6/1968 | Maruta et al. | |
| 3,930,032 A | 12/1975 | Harris et al. | |
| 4,678,672 A | 7/1987 | Dartey et al. | |
| 5,468,716 A | 11/1995 | Winston | |
| 5,472,476 A | 12/1995 | Schapira et al. | |
| 5,482,702 A | 1/1996 | Murphy et al. | |
| 2002/0018836 A1 | 2/2002 | Diener et al. | |
| 2005/0118326 A1 | 6/2005 | Anfinsen et al. | |
| 2005/0233046 A1 | 10/2005 | Krawczyk et al. | |
| 2009/0317531 A1 * | 12/2009 | Reh et al. | 426/563 |

FOREIGN PATENT DOCUMENTS

| | | |
|---|---|---|
| CA | 2016961 A1 | 11/1990 |
| DE | 2435008 A1 | 2/1975 |
| DE | 117 787 | 2/1976 |
| DE | 2821703 A1 | 11/1978 |
| EP | 246719 A2 | 11/1987 |
| EP | 399995 A1 | 11/1990 |
| EP | 461886 A1 | 12/1991 |
| EP | 1161872 A2 | 12/2001 |
| EP | 1260147 A2 | 11/2002 |
| GB | 745926 A | 3/1956 |
| GB | 1 483 591 A | 8/1977 |
| GB | 1596076 A | 8/1981 |
| SU | 1570255 A1 | 11/1992 |
| WO | WO-94/24860 A1 | 11/1994 |
| WO | WO-94/24994 A1 | 11/1994 |
| WO | WO-97/12607 A1 | 4/1997 |
| WO | WO-98/56595 A1 | 12/1998 |
| WO | WO-01/5246 A2 | 1/2001 |
| WO | WO-2004/048418 A2 | 6/2004 |

* cited by examiner

*Primary Examiner* — Jessica Worsham
(74) *Attorney, Agent, or Firm* — Drinker Biddle & Reath LLP

(57) ABSTRACT

The present invention relates to mixed crystals comprising a) leavening agent and b) 0.1 to 5000 ppm by weight of crystallization aid, based on the total amount of the leavening agent, in the form of at least polymer, wherein when hydrophilic cellulose derivatives are used as crystallization aid, the amount thereof is reduced to less than 100 ppm by weight, based on the total amount of the leavening agent. The present invention further relates to the production of the mixed crystals and to the use thereof in the production of bakery products, as acid regulator in foods, in the production of cosmetics products, in the synthesis and formulation of pharmaceutical products, and also as blowing agent in industrial processes such as, for example, the production of foam rubber, or for fire-extinguishing formulations. The present invention relates, furthermore, to the production of bakery products.

15 Claims, 10 Drawing Sheets

A:

B:

A:

B:

C:

A:

B:

A:

B:

A:

B:

A:

B:

MIXED CRYSTALS, METHOD FOR THE PRODUCTION THEREOF AND USE THEREOF IN THE PRODUCTION OF BAKED GOODS

CROSS-REFERENCE TO RELATED APPLICATIONS

This application is a national stage application (under 35 U.S.C. § 371) of PCT/EP2009/067301, filed Dec. 16, 2009, which claims benefit of European application 08172799.2, filed Dec. 23, 2008.

BACKGROUND OF THE INVENTION

The present invention relates to mixed crystals comprising a) leavening agent and b) 0.1 to 5000 ppm by weight of crystallization aid, based on the total amount of the leavening agent, in the form of at least polymer, wherein when hydrophilic cellulose derivatives are used as crystallization aid, the amount thereof is reduced to less than 100 ppm by weight, based on the total amount of the leavening agents. The present invention further relates to the production of the mixed crystals and to the use thereof in the production of bakery products, as acid regulator in foods, in the production of cosmetics products, in the synthesis and formulation of pharmaceutical products, and also as blowing agent in industrial processes such as, for example, the production of foam rubber, or for fire-extinguishing formulations. The present invention relates, furthermore, to the production of bakery products.

For the production of porous bakery products, a gas is generated in the dough before and/or during the baking process, or the dough is admixed with gas in order to generate porosity in the baked product by virtue of the gas bubbles. In the simplest scenario, the dough is admixed, prior to baking, with a gas, usually air, for instance by intense beating of the dough or of one of its ingredients prior to mixing. The most well-known embodiment is the addition of beaten egg white to the dough. It is equally possible to incorporate a gas such as air into the dough through nozzles. Also known are methods in which steam loosens the dough, as in the production of flaky pastry. The gas usually used, however, is carbon dioxide, or carbon dioxide in a mixture with ammonia and steam. Carbon dioxide is generated, for example, biologically in the course of the fermentation of dough ingredients by yeasts (yeast dough) and/or by lactic acid bacteria (sour dough). Alternatively or additionally to the use of yeast or sour dough, carbon dioxide, or the carbon dioxide, ammonia and steam mixture, is also generated chemically by means of baking additives, known as leavening agents or, in common parlance, as "baking powders" which are added to the dough.

Leavening agents generally comprise at least one carbonate and, if it does not decompose solely due to temperature increase, an acidic or acid-forming substance. Optionally, in addition to carbonate, they also comprise carbamate. The carbonate and/or carbamate is selected in line with the baked article to be produced; for spiced cake or honey cake, for example, potassium carbonate is frequently used, while for flat bakery products it is common to use sodium hydrogencarbonate (former name: "sodium bicarbonate"), ammonium hydrogencarbonate ("ammonium bicarbonate" "ABC" for short), as sole carbonate or in a mixture with ammonium carbamate ("ammonium carbonate"). The acid or the acid-former must not adversely affect the taste, either itself or together with the nonvolatilizing residues of the carbonate or carbamate. Typically, compounds are used such as tartaric acid or its salts, such as potassium, sodium, potassium hydrogen and/or calcium tartrate, citric acid, calcium hydrogenphosphate, sodium hydrogen pyrophosphate or sodium aluminum phosphate. If the leavening agent comprises an acid or an acid-former, it is usually admixed with a release agent which prevents the premature formation of carbon dioxide by reaction of the carbonate with the acid or acid-former, the addition of flour or starch being customary for this purpose. The aforementioned ammonium compounds ABC and ammonium carbamate decompose solely due to temperature increase at not less than 60° C., without residue, to form carbon dioxide, ammonia, and water. At typical baking temperatures, all three components are obtained in gaseous form, and therefore all result in an increase in the porosity of the baked product. These compounds are typically used, consequently, without an added acid or acid-former, and so there is no need to add the release agent.

Ullmanns Encyklopädie der technischen Chemie, $3^{rd}$ edition, Urban & Schwarzenhäuser, Munich—Berlin 1953, head words "Backpulver" [baking powder], or Ullmann's Encyclopedia of Industrial Chemistry, Sixth ed., 1999 Electronic Release, Wiley-VCH, Weinheim 1999, head word "Bread and other baked Products", section 2.6 therein: "Leavening Agents", provide a comprehensive overview of the known methods of producing porous bakery products using leavening agents. The preparation of ammonium compounds such as ammonium carbonate, bicarbonate, and carbamate by reaction of quantities of ammonia and carbon dioxide corresponding to the desired product, in aqueous mother liquor, at pressures and temperatures selected in line with the product, followed by removal and drying of the precipitate, has also been known for a long time and is described in, for example, Ullmann's Encyclopedia of Industrial Chemistry, sixth edition, 1999, Electronic Release, Wiley-VCH, Weinheim 1999, head word "Ammonium Compounds", especially section 4: "Ammonium Carbonates". The preparation of alkali metal carbonates and hydrogen carbonates is known as well.

Although these ammonium compounds are obtained in gaseous form at typical baking temperatures, it is common to add an anticaking agent to the leavening agent, in order to prevent the formation, referred to as "caking", of lumps or sizable agglomerates in the powdery leavening agent. Anticaking agents used for this purpose are typically cornflour, magnesium oxide or magnesium carbonate in an amount of 2000 to 10 000 ppm by weight, based on the leavening agent. Optionally, in addition, inorganic salts are mixed with the anticaking agents.

The purpose of the anticaking agent, consequently, is to prevent the caking of the leavening agent that typically occurs under storage conditions. Instances of caking represent a major problem, particularly in the case of storage under pressure. These caked lumps are often difficult to loosen, and lumps remain in spite of loosening. The consequences of the caked-together lumps of leavening agent that remain are, primarily, unwanted, large gas bubbles during the baking process, and therefore large cavities in the baked article. These large cavities frequently go well beyond the desired pore diameter of 0.1 to about 5 mm for the pores in the baked article. This results in an undesirably high reject rate, since such baked articles, although containing individual cavities that are very large, otherwise consist predominantly of regions with an undesirably low porosity, and this makes the baked article hard and often visually unattractive as well. If the large cavities occur on the surface of the baked article, the layer of dough at the top, which is then thin, will bake substantially more quickly during the baking process, and will then have an unattractive dark brown or black discoloration. These bakery products are then unsaleable and increase the reject rate in production.

EP-A 1 161 872 discloses the use of anticaking agents based on hydrophilic cellulose derivatives. Sodium carboxymethylcelluloses are cited as preferred hydrophilic polymeric cellulose derivatives. There is disclosure to the effect that the cellulose derivative is used in an amount of at least 100 ppm by weight, based on the total amount of the leavening agent, more preferably at least 500 ppm by weight, with 1000 ppm by weight for example. EP-A 1 161 872 describes how the anticaking agent is added during or after the crystallization of the leavening agent, to the mother liquor. If the anticaking agent is added after the crystallization of the leavening agent, then leavening agent crystals form that are enveloped with anticaking agent—in other words, the crystals of leavening agent have an outer coat of anticaking agent. These coated leavening agents have a significantly reduced caking tendency as compared with uncoated leavening agents. In the case of storage under pressure, however, the anticaking agent coat is unable sufficiently to prevent caking (see example 5). If the anticaking agent is added during the crystallization of the leavening agent, then rod-shaped mixed crystals of leavening agent and anticaking agent are formed (see FIG. 4C). On account of the rod-shaped crystal morphology and hence a large contact area between the individual mixed crystals, however, the caking propensity of these mixed crystals is high (see example 4).

The use of cellulose derivatives and pectin within the food industry is multifaceted:

Hydrophilic cellulose derivatives are used in bakery products not only as anticaking agents but also, furthermore, as bulk-forming materials in an amount of, typically, 5% to 20% by weight, based on the bakery product (U.S. Pat. No. 4,678,672 and GB 745,926). Also known is the use of carboxymethylcellulose as a thickener in a typical amount of 0.5% to 1% by weight, based on the bakery product (EP-A 399 995).

US 2005/233046 describes stabilizers composed of microcellulose and hydrocolloid, e.g., pectin, in a weight ratio of 30/70 to 90/10. Optionally a salt is added, calcium chloride or potassium carbonate, for example, in an amount of 0.5% to 5% by weight. The use of these stabilizers in the production of foods is disclosed.

WO 01/5246 describes a method of producing compositions comprising at least one emulsifier and at least one bulk-forming substance. It is preferred to use compositions which additionally influence emulsifier, comprising, for example, a mixture of pectin and carrageenan in a weight ratio of 20:80 to 40:60, and a mixture of pectin and guar gum in a weight ratio of 30:70 to 70:30, and a leavening agent as well.

The prior art contains numerous disclosures of leavening agents covered with a protective film (a coat) of any of a very wide variety of anticaking agents. Described as a protective film, for example, are polysaccharides and derivatives thereof, more particularly starch, cellulose, manna, sodium alginate, methylcellulose, carboxymethylstarch, and carboxymethylcellulose (DE-A 28 21 703, WO 98/56595). Also used for coating particles are water-soluble cellulose esters (EP-A 461 886) or film-forming polymers such as methylcellulose, hydroxybutylmethylcellulose, sodium carboxymethylcellulose, hydroxyethylmethylcellulose or hydroxypropylmethylcellulose (DE-A 24 35 008). Optionally it is possible to use further anticaking agents such as magnesium silicate (WO 94/24860, U.S. Pat. No. 5,482,702) or phosphorous compounds (U.S. Pat. No. 5,468,716).

Part of the reason for the caking of the common leavening agents is the crystal morphology of the products. As a result of accretions and other crystal defects, the salts that are readily available industrially have a very rough structure. On account of the rough structure, these crystal forms may very easily become intermeshed, and mechanically stable bridges are formed between the individual crystals. These stable bridges produce the known high caking propensity in the products. FIG. 1 depicts an ammonium bicarbonate agglomerate, used typically as a leavening agent in the prior art.

The protective coat described (outer coat/shell) causes rounding of the otherwise rough crystal shape (see FIG. 1), by covering the crystal peaks and crystal accretions, and filling out the interstices, in order to reduce the intermeshing and hence agglomeration of the leavening agent crystals. The anticaking agent is used, consequently, as a spacer or for coating the rough crystal structure in order to round it off.

In all of the following specifications, fully crystallized, usually commercially available leavening agents are used, which, following crystallization of the leavening agent, are covered with an anticaking agent.

In summary, in the prior art set out below, the system which is present does not comprise mixed crystals of two or more substances, but instead comprises a pure crystal which has been coated/enveloped. As already described in the case of EP-A 1 161 872, coated leavening agents do have a significantly reduced caking tendency as compared with uncoated leavening agents. In the case of storage under pressure, however, the anticaking agent coat is unable sufficiently to prevent caking (see examples 2 and 3).

U.S. Pat. No. 3,930,032 discloses the coating of leavening agents with cellulose ethers for increasing the stability of the leavening agent. The leavening agent coated with cellulose ethers contains 3% of cellulose derivative.

EP-A-1 260 147 discloses a matrix of active components, examples being alkali metal or alkaline earth metal carbonates, and a polymeric material such as, for example, polysaccharides or cellulose. The weight ratio in the matrix of active component to polymer is 1:99 to 99:1, more particularly 40:60 to 60:40. Accordingly, the minimum level of the use of the polymer lies at 1% by weight of polymer, based on the alkali metal or alkaline earth metal carbonate.

WO 2004/48418 describes the preparation of carboxymethylcellulose (CMC) and the use of CMC in the production of bakery products. Example 16 describes a dough comprising, among other ingredients, sodium carbonate and CMC prepared in accordance with example 9. In relation to the dry dough, 0.9% by weight of sodium carbonate and 0.3% by weight of CMC are used, in other words 33% by weight of CMC in relation to the leavening agent.

U.S. Pat. No. 1,643,951 describes bakery products, more particularly meringues, comprising water-soluble pectin jelly. Bakery product dough compositions are described which include 5% by weight of pectin and 2% by weight of sodium carbonate, i.e., 250% by weight of pectin in relation to the leavening agent.

U.S. Pat. No. 2,791,508 describes the production of chips using algin or pectin. The examples in D5 disclose chip dough compositions comprising algin or pectin and calcium carbonate in a weight ratio as follows: (a) 1:0.12; (b) 1.75:0.12; and (c) 1:0.04, i.e., 800% to 2500% by weight of pectin or algin in relation to the leavening agent.

US 2005/118326 describes highly digestible foods. Example 6 describes a dough for tortillas, containing 0.28% of leavening agent, 1% of xanthan, and 0.3% of pectin, i.e., 464% by weight of polymer (xanthan and pectin) in relation to the leavening agent.

WO 97/12607 describes the encapsulation of alkali metal carbonates with an organic hydrophilic shell of, for example, xanthan or pectin. The organic shell makes up 5% to 60% by weight of the encapsulated alkali metal carbonates, i.e., about 5% to 150% by weight of polymer (e.g., xanthan or pectin) in relation to the leavening agent.

WO 94/24994 describes particles comprising a core of alkali metal carbonates or ammonium carbonates and a shell of hydrophilic polymers. Pectin or xanthan is described for example as polymer. The polymer coating accounts for 5% to 50% by weight of the dry coated particles, i.e., about 5% to 100% by weight of polymer (e.g., xanthan or pectin) in relation to the alkali metal carbonates/ammonium carbonates.

The use of anticaking agents is also widespread in fertilizers, since the fertilizers have to be comparatively stable in storage, as a result of their seasonal use.

Additionally used as anticaking agents, for example, are glues based on carboxymethylcellulose, mixed with fillers such as calcium carbonate or calcium oxide (DD-A 117 787); synthetic polymers such as, for example, carboxymethylcellulose or methylcellulose and a surface-active substance (U.S. Pat. No. 3,388,990/U.S. Pat. No. 5,472,476), hydroxypropylcellulose, sodium carboxymethylcellulose or hydroxypropylmethylcellulose (EP-A 246 719); or sodium carboxylmethylcellulose and a surface-active substance (SU-A 1570255).

To summarize, a disadvantage of the prior art is that, with the known measures for preventing the caking propensity, caking in storage under pressure cannot be adequately prevented. Consequently, these leavening agents have to be loosened in a separate step before use. Unfortunately, despite the loosening, caked lumps of the leavening agent remain, and lead to the formation of undesirably large gas bubbles and, consequently, of undesirably large cavities in the baked article.

Furthermore, mixtures of leavening agent and anticaking agent for use in continuous operation for the production of bakery products (automated baking lines) are disadvantageous. These mixtures are typically introduced in powder form via a metering means. In order to prevent caking of the mixture in the metering means, said means is continuously shaken. This shaking, however, causes separation of the leavening agent and the anticaking agent. The anticaking agent is therefore no longer present uniformly in the leavening agent, and there may be instances of caking of the leavening agent and hence of unwanted formation of ununiformly large cavities in the baked article. As a result, there is a risk of increased rejection.

A further disadvantage of the leavening agents from the prior art is their poor shelf life. Particularly in the context of the storage under pressure that is usual in this field of application, the prior art records instances of caking after just a few days, for both the coated leavening agents and for the pure powdery mixture of leavening agent and anticaking agent. Storage under pressure is usual, since lack of space dictates that the bags in question are stored on top of one another.

Accordingly, in spite of the use of anticaking agents and/or of a protective coating on the leavening agents, there are instances of caking, in other words of formation and lumps or sizable agglomerates, in the course of the storage and the use of leavening agents, and this continues to constitute an resolved problem. The caked lumps cause the formation of undesirably large cavities and hence an ununiform distribution of cavities.

BRIEF SUMMARY OF THE INVENTION

It is an object of the present invention, therefore, to provide a modified leavening agent which in comparison to the prior art is less readily agglomerated and/or has agglomerates which can easily be loosened again. Furthermore, in comparison to the prior art, the aim for the first time is to modify the cause of the agglomeration, i.e., the crystal morphology of the leavening agent, instead of merely minimizing the effects of the crystal morphology. Furthermore, in spite of use of only very small amounts of aid, this modified leavening agent is to form, even on long storage, a free-flowing, flowable powder, which remains precisely meterable when used on automated/continuous baking lines. In the production of bakery products, more particularly, the formation of undesirably large cavities is to be avoided.

Surprisingly it has been found that mixed crystals comprising
a) leavening agent
b) 0.1 to 5000 ppm by weight (0.00001% to 0.5% by weight) of crystallization aid, based on the total amount of the leavening agent, in the form of at least one polymer, it also being possible for mixtures of different polymers to be used, wherein when hydrophilic cellulose derivatives are used as crystallization aid, the amount thereof is reduced to less than 100 ppm by weight (<0.01% by weight), based on the total amount of the leavening agent,
have a uniform and noncaking crystal structure.

A BRIEF DESCRIPTION OF THE DRAWINGS

Figure 3:
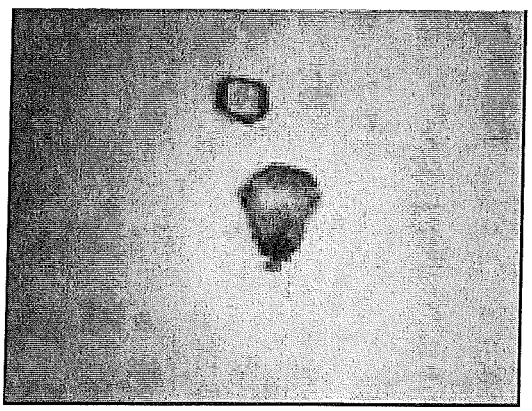
Figure 3:
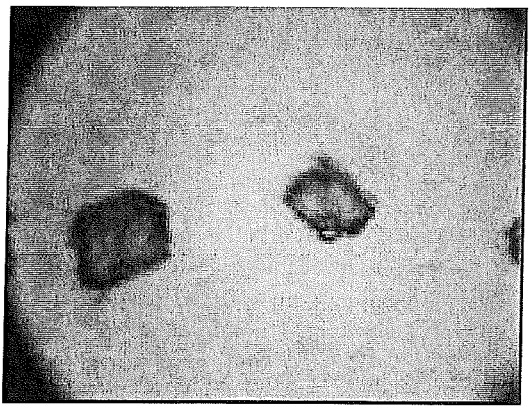

FIGS. 3 A/B, 4 A/B, and 5 illustrate that the mixed crystals of the invention have a uniform, round, smooth, and hence noncaking crystal structure.

FIG. 4C illustrates where hydrophilic cellulose derivatives are used as crystallization aids, unwanted formation of rod crystals rather than spherical crystals is obtained from a level even of about 100 ppm by weight upward.

Figure 6:
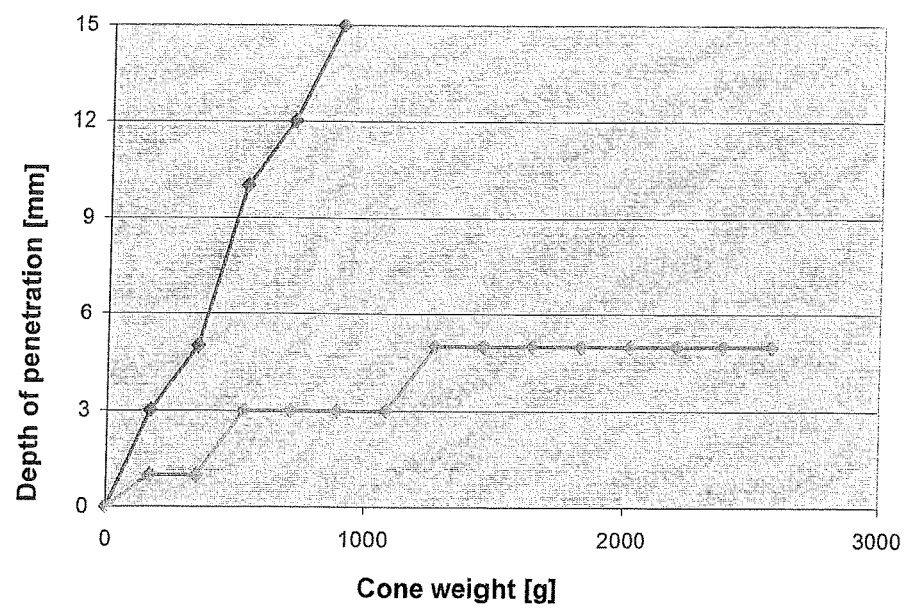

FIG. 6 illustrates the results shown in Table 2

FIG. 7A illustrates the prior art ABC which has undergone severe caking, and relatively large lumps remain even when the powder is moved (loosening attempts).

Figure 7:
Figure 7:
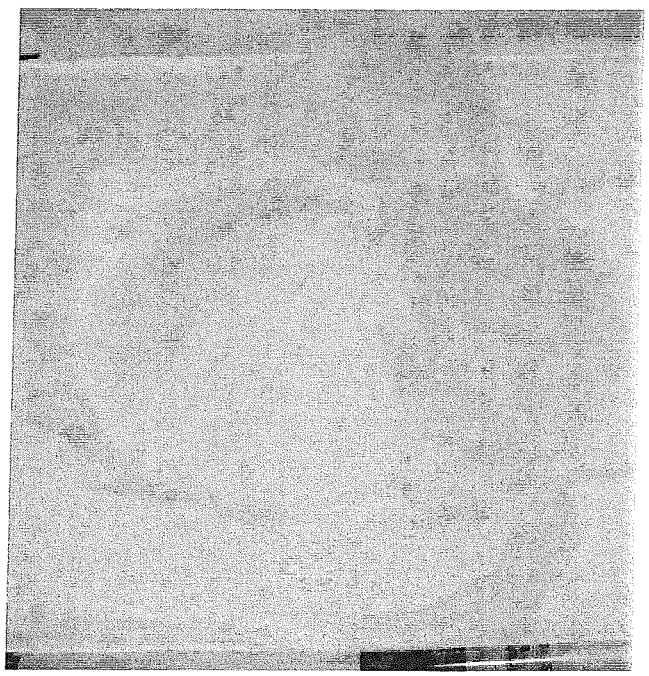

FIG. 7 B illustrates the mixed crystals of the invention, with pectin, which are very readily flowable and absolutely lump-free.

FIG. 8A illustrates the prior art ABC which has undergone very severe caking, and large, solid lumps remain even when the bag is knocked.

Figure 8:
Figure 8:

FIG. 8 B illustrates the mixed crystals of the invention, with pectin, are readily flowable. The small lumps disappear when the product is moved.

FIG. 9A illustrates the prior art ABC which has undergone severe caking.

FIG. 9B the mixed crystals with pectin which are readily flowable, without the formation of lumps.

Figure 10:
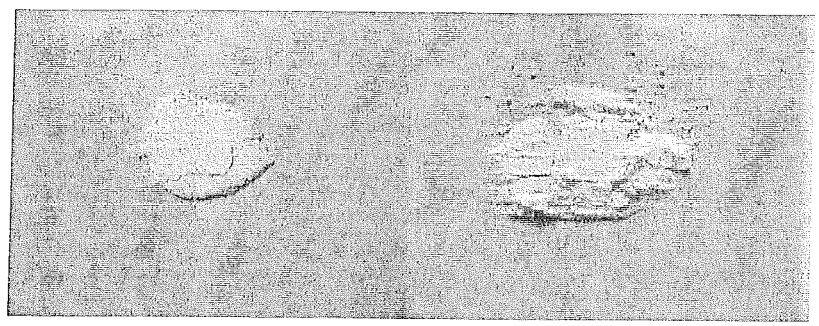
Figure 10:
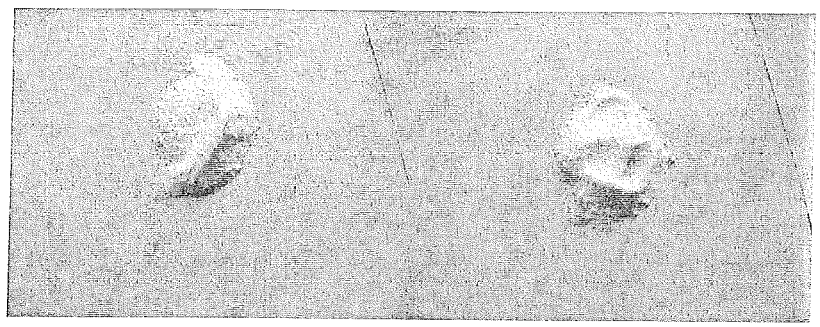

FIG. 10A illustrates ABC with 100 ppm Tylose (comparative example in analogy to EP 1 161 872).

FIG. 10B the mixed crystals with 25 ppm Tylose.

DETAILED DESCRIPTION OF THE INVENTION

The term "mixed crystal" in the present invention refers to a crystal which consists of at least of two different chemical elements or substances. These extraneous substances may alternatively be lodged in the lattice interstices, replace an atom or substance group of the other element by substitution, or be present on the crystal surface. In order to obtain a mixed crystal, it is mandatory for the at least two elements or substances to be present during the crystallization of the mixed crystal (e.g., in the crystallization mother liquor). The crystallization aid (component b) is located, accordingly, in and/or on the leavening agent crystal (component a), i.e., in the crystal and/or on the crystal surface.

The mixed crystals of the invention, accordingly, constitute a modified leavening agent.

The mixed crystals of the invention are advantageously loosenable or flowable after storage for a month under a load of one tonne. Preferably, the mixed crystals of the invention are loosenable or flowable after storage for two months, preferably four months, more particularly six months, very preferably twelve months, after a load of one tonne, preferably two tonnes, more particularly four tonnes.

The term "flowable" in the context of the present invention means that the stored product is lump-free (caking-free) after storage, for example, or transport in bags, after the bags have been opened, and constitutes a free-flowing powder (exhibiting free mobility and flow behavior). In illustrative terms, "flowable" means that the product, after the bags are opened, does not fall out of the bags in the form of one or more clumps (having undergone severe lumping), but instead flows/trickles freely from the bags.

The term "loosenable" in the context of the present invention means that after 1 to 5 loosening attempts, preferably after 1 to 3, more particularly after only one loosening attempt, the stored product is flowable and therefore lump-free; a loosening attempt in this context entails a single dropping of the product-filled bags (typically 25 kg) from a height of 1.5 m. Plural loosening attempts, accordingly, denote repeated dropping of the product-filled bags.

The term "lump-free" in the context of the present invention means that the flowable powder is free from agglomerates which have formed in the course of storage.

The mixed crystals of the invention have a uniform, round, smooth, and hence noncaking crystal structure (see FIGS. 3 A/B, 4 A/B, and 5). The mixed crystals of the invention are generally compact, without pointed accretions on the crystal surfaces. Consequently, the mixed crystals of the invention are unable to intermesh with one another (undergo caking). As a result of the rounded surfaces, moreover, caking is unlikely, even under relatively high pressure, since there is no contact area between two spherical crystals, but instead only a contact point.

Under a pressure load, crystals with pointed accretions form large and very firm packed structures, owing to the high contact area. The same effect occurs with crystals having a rodlet form, since they have very large contact areas between the crystals, unlike the spherical mixed crystals of the invention.

Even a slight mechanical loading (loosening attempt) separates the mixed crystals of the invention, but the separation of agglomerates of rodlet-shaped crystals or crystals with accretions is no longer possible.

On account of the compact, relatively uniform, round crystal morphology, storage and application are accompanied by the formation of caked lumps and agglomerates that are substantially fewer in number and, moreover, are easier to loosen again than in the case of leavening agents from the prior art.

The leavening agent (component a) comprises at least one carbonate. Selected as carbonate are carbonates whose use in foods is unobjectionable and which, both as themselves and as their decomposition products, do not result in an unpleasant taste in the bakery products. Suitable carbonates, present individually or in a mixture, are known to the skilled person, and, typically, alkali metal carbonates and hydrogencarbonates, more particularly sodium carbonate, sodium hydrogencarbonate, potassium carbonate and potassium hydrogencarbonate, and ammonium carbonate and ammonium hydrogencarbonate are used.

Also suitable is the mixture of ammonium carbonate and ammonium hydrogencarbonate which is referred to customarily as "salt of hartshorn" and which may also contain ammonium carbamate as well.

The carbonate is preferably ammonium hydrogencarbonate and/or ammonium carbonate. With particular preference the carbonate is ammonium hydrogencarbonate (also called ammonium bicarbonate, ABC for short).

The average particle diameters of the carbonates used are generally 50 to 1000 µm, preferably 75 to 700 µm, more preferably 150 to 500 µm.

The leavening agent optionally further comprises one or more carbamates. Selected as carbamate are carbamates whose use in foods is unobjectionable and which, both as themselves and as their decomposition products, do not result in an unpleasant taste in the bakery products. One suitable carbamate is ammonium carbamate, for example.

If the leavening agent contains carbamate, the amount of carbamate is preferably 10% to 90% by weight, based on the total amount of the leavening agent, more preferably 30% to 70% by weight, more particularly about 50% by weight. The mixture of equal parts of ammonium carbamate and ammonium bicarbonate is also referred to as ammonium carbonate.

If the leavening agent used includes components which on heating to typical baking temperatures of 100 to 200° C., for example, do not decompose or do not decompose sufficiently, it is advantageous for the leavening agent further to comprise an acid or an acid-former. The acid or acid-former is a compound or mixture of compounds known for this utility, examples being potassium, sodium, potassium hydrogen and/or calcium tartrate, citric acid, calcium hydrogenphosphate, sodium hydrogenpyrophosphate and/or sodium aluminum phosphate. If the leavening agent includes acid or acid-former, the amount of acid or acid-former is preferably as much as is needed for the reaction of the leavening agent and hence for the release of carbon dioxide. Depending on acid strength, number of protons per molecule, and molar weight of the acid and of the leavening agent, this amount may differ greatly. As an example, when using sodium bicarbonate and for customary acid carriers, a range from 60% to 250% by weight is the case, based on the total amount of the leavening agent, preferably 75% to 225% by weight.

If the leavening agent includes an acid or an acid-former, it is preferably admixed with a release agent as well, which prevents the premature formation of carbon dioxide through reaction of the carbonate with the acid or acid-former. Release agents of this kind are known, preference being given to flour and/or starch.

The average particle diameters of the acids or acid-formers used is generally 50 to 1000 µm, preferably 75 to 700 µm, more preferably 150 to 500 µm.

The stated carbonates, carbamates, acids or acid-formers, and also release agents, are available commercially.

The crystallization aid (component b) preferably comprises at least one crystallization-influencing polymer. The term "crystallization-influencing" is understood in the present invention to mean that the added polymer influences the crystal morphology of the resultant crystals in a suitable way. Under the action of the crystallization-influencing polymers, the leavening agent crystals exhibit a smooth and regular structure. This structure is in contrast to the crystal structure without crystallization-influencing polymer, which is characterized by disruptive accretions and different crystal morphologies with an irregular and rough surface.

Furthermore, the polymer is preferably hydrophilic. It is possible to use uncharged, anionic and/or cationic crystallization-influencing polymers.

Furthermore, besides individual polymers, it is also possible for mixtures of different uncharged, different anionic and/or different cationic polymers to be used. Besides these, uncharged polymers may also be used as mixing components for anionic and/or cationic polymer mixtures.

For obvious reasons, these polymers are advantageously selected such that not only the polymer itself but also any thermal breakdown products, in the amounts typically present or formed, are suitable as food additives and do not adversely affect the taste of the bakery products produced. It is preferred to use polymers of natural origin or those formed by modification of natural polymers, with a neutral taste and with approval under food law.

Preferred charged natural polymers are hydrophilic polymers based on sugar derivatives and/or peptides, more particularly from the areas of the (hetero)polysaccharides and/or (poly)peptides.

These heteropolysaccharides are obtained typically by fermentation or by isolation from natural sources.

Particularly preferred are charged (hetero)polysaccharides with carboxyl or sulfonate side chains, more particularly with nonmodified carboxyl groups (e.g., pectin and/or alginate) and with modified carboxyl groups (e.g., amidated pectin).

Advantageous anionic polymers are, for example, polyacrylic acid and salts thereof with ammonium, sodium or potassium, polymethacrylic acid and salts thereof with ammonium, sodium or potassium, acrylic acid and salts thereof with ammonium, sodium or potassium, methacrylic acid copolymers and salts thereof with ammonium, sodium or potassium, and acrylic acid-maleic acid copolymers and salts thereof with ammonium, sodium or potassium.

The stated anionic polymers may further comprise vinylsulfonic acid in variable proportions.

All of the stated anionic polymers may have partially esterified groups, in which case not only aliphatic components but also derivatized components based on endgroup-capped polyalkylene glycols may be present as alcohol components. For the preparation of the polyalkylene glycols it is possible to use not only ethylene oxide but also propylene oxide and higher alkylene oxides, alone or in the form of random or block polymers.

Preference is given, furthermore, to polyaspartite acid and the salts thereof with monovalent and divalent cations. Particularly preferred are the salts of polyaspartite acid with ammonium, sodium, and potassium.

Advantageous cationic polymers are, for example, polyamines, polyvinylamines and copolymers with polyvinyl alcohol and/or polydimethylallylammonium chloride.

Advantageous nonionic polymers are, for example, polyethylene glycols, polypropylene glycols, random and block polymers based on ethylene oxide with alkylene oxides, more particularly propylene oxide and/or butylene oxide. Optionally, these polymers further comprise an additional endgroup cap on one or both sides, with aliphatic endgroups. Preference is given, furthermore, to polyvinylvinylpyrrolidone and/or polyvinylpolypyrrolidone.

Preferred more particularly are those polymers which already have approval as food additives, such as, for example, the following: alginic acid (E 400), sodium alginate (E 401), potassium alginate (E 402), ammonium alginate (E 403), calcium alginate (E 404), propylene glycol alginate (E 405), agar-agar (E 406), carrageenan (E 407), processed Eucheuma algae (E 407a), carob bean meal (E 410), guar seed meal (E 412), tragacanth (E 412), gum arabic (E414), xanthan (E 415), karaya (E 416), tara gum (E 417), gellan (E 418), konjak gum/konjak glucomannan (E 425), soybean-polyose (E426), pectin/amidated pectin (E 440), microcrystalline cellulose/cellulose powder (E 460), methylcellulose (E 461), ethylcellulose (E 462), hydroxypropylcellulose (E 463), hydroxypropylmethylcellulose (E 464), ethylmethylcellulose (E 465), carboxymethylcellulose/sodium carboxymethylcellulose (E 466), crosslinked sodium carboxymethylcellulose (E 468), enzymatically hydrolyzed carboxymethylcellulose (E 469), polydextrose (E 1200), polyvinylpyrrolidone (E 1201), polyvinylpolypyrrolidone (E 1202), pullulan (E 1204), oxidized starch (E 1404), monostarch phosphate (E 1410), distarch phosphate (E 1412), phosphated distarch phosphate (E 1413), acetylated distarch phosphate (E 1414), acetylated starch (E 1420), acetylated distarch adipate (E 1422), hydroxypropylstarch (E 1440), hydroxypropyldistarch phosphate (E 1442), starch sodium octenyl succinate (E 1450), acetylated oxidized starch (E 1451).

Particularly preferred are crystallization aids selected from the group consisting of alginic acid (E 400), sodium alginate (E 401), potassium alginate (E 402), ammonium alginate (E 403), calcium alginate (E 404), propylene glycol alginate (E 405), pectin (E440), amidated pectin (E440), carrageenan (E 407), gellan (E418), gum arabic (E414), karaya (E 416), tragacanth (E 412), xanthan (E 415), and/or gellan (E 418); especially preferred are crystallization aids selected from the group consisting of alginic acid (E 400), sodium alginate (E 401), ammonium alginate (E 403), pectin (E 440), amidated pectin and/or gellan (E418); more particularly preferred are pectin (E 440) and/or amidated pectin (E 440).

Further preferred as crystallization aids are linear and/or branched (poly)peptides. Particularly preferred in the area of the (poly)peptides are gelatin products.

Suitable cellulose derivatives are, for example, cellulose ethers. These are cellulose derivatives which originate formally by substitution of hydrogen atoms on the hydroxyl groups of the cellulose by alkyl groups and/or arylalkyl groups, it being possible for these alkyl and/or arylalkyl groups to be substituted by functional nonionic, anionic and/or cationic groups. The alkyl groups are typically C1-C8 alkyl groups, which may be linear or branched. The alkyl group is preferably a C1-C4 alkyl group, examples being methyl, ethyl, n-propyl, isopropyl, n-butyl, sec-butyl, isobutyl or tert-butyl. The alkyl group may be substituted by an aromatic radical to form the arylalkyl group, such as with a phenyl radical, for example. One preferred arylalkyl group is benzyl. The alkyl or arylalkyl group may be functionally substituted, by hydroxyl, carboxyl or carboxylate groups, for example. Where carboxylate groups are present, corresponding counterions are present as well, examples being alkali metal ions such as sodium or potassium, or ammonium ions.

Where reference is made only to "carboxymethylcellulose" (often abbreviated to "CMC"), the compound meant is usually sodium carboxymethylcullose (occasionally also abbreviated to "Na-CMC"). It is also possible to use mixed cellulose ethers, which contain more than one kind of alkyl, arylalkyl or functionally substituted alkyl groups.

Preferred hydrophilic polymeric cellulose derivatives are methyl-, ethyl-, propyl-, carboxymethyl-, hydroxyethyl-, hydroxypropyl-, methylhydroxyethyl-, methylhydroxy-propyl-, methylhydroxybutyl-, ethylhydroxydethyl-, carboxymethylhydroxyethyl- and/or benzyl-cellulose. Among the carboxymethylcelluloses, the sodium compound is preferred. The leavening agent preferentially comprises sodium carboxymethylcellulose.

The cellulose ethers are prepared in a known way, typically by the action of alkyl halides or arylalkyl halides, epoxides or activated olefins on cellulose that has been activated with bases (aqueous sodium hydroxide solution, for example). Cellulose ethers are commonplace commercial products which are used typically—in foods as well—as thickeners. Cellulose ethers are available, for example, under the brand name "Tylose", while high-purity cellulose ethers for food applications are available under the brand name "Tylopur", and high-purity Na-CMC under the brand name "Tylopur C" from Clariant GmbH.

Counterions contemplated, in addition to hydrogen, are alkali metal ions and/or alkaline earth metal ions, and also substituted or unsubstituted amines, ammonia being an example.

The preparation of the stated polymers is common knowledge and can be read up in common technical literature.

The mixed crystals comprise the crystallization aid preferably in an amount of 0.5 to 5000 ppm by weight (0.00005% to 0.5% by weight), based on the leavening agent, preferably from 0.5 to 2000 ppm by weight (0.00005% to 0.2% by weight), more preferably from 1 to 1000 ppm by weight (0.0001% to 0.1% by weight), more particularly from 1 to 500 ppm by weight (0.0001% to 0.5% by weight), very preferably from 1 to 100 ppm by weight (0.0001% to 0.01% by weight), furthermore preferably from 1 to 50 ppm by weight (0.0001% to 0.005% by weight), additionally preferably from 1 to 20 ppm by weight (0.0001% to 0.002% by weight).

If hydrophilic cellulose derivatives are used as crystallization aids, the amount of hydrophilic cellulose derivatives in the leavening agent is preferably less than 80 ppm by weight (<0.008% by weight), based on the leavening agent, preferably between 0.5 and 50 ppm by weight (0.00005% to 0.005% by weight), more particularly between 1 and 20 ppm by weight (0.0001% to 0.002% by weight).

Figure 1:
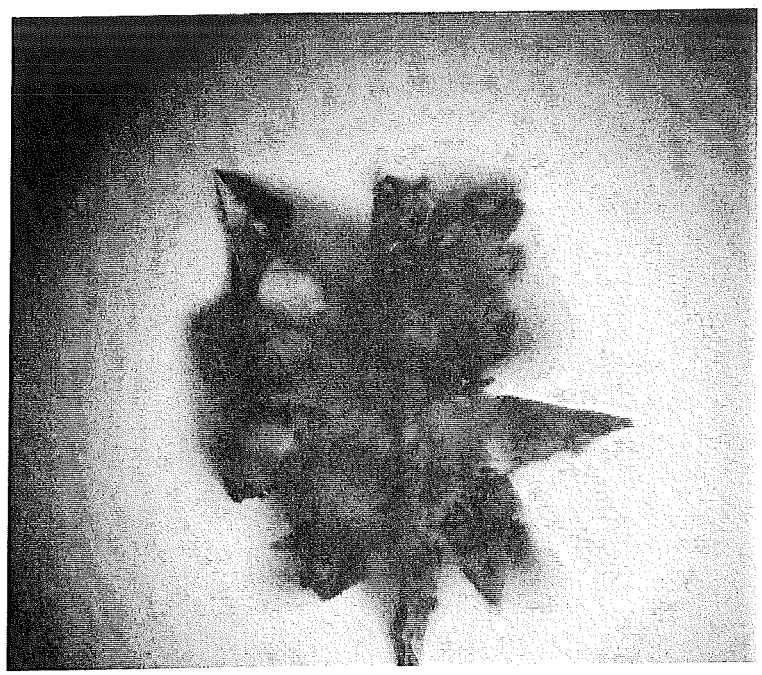
FIG. 1 depicts an ammonium bicarbonate agglomerate, used typically as a leavening agent in the prior art.

Increasing the amount of crystallization aid beyond a maximum level leads to adverse effects on the desired crystal modification and crystallization propensity. Where hydrophilic cellulose derivatives are used as crystallization aids, unwanted formation of rod crystals rather than spherical crystals is obtained from a level even of about 100 ppm by weight upward (see FIG. 4C). These rod crystals in turn have a tendency to intermesh and hence to undergo caking (see example 4), in a similar way to the ammonium bicarbonate from the prior art (see FIG. 1). In addition, they become moist are a certain time, and then form a sticky mass.

Using more than 5000 ppm by weight of crystallization aid produces predominantly very large crystals and/or crystals having relatively rough surfaces. The large crystals would then have to be ground before being used. Grinding would denote an additionally, cost-intensive step which, furthermore, harbors the risk of production of particles with rough surfaces.

The present invention further provides the method for producing the mixed crystals of the invention, which comprises adding the crystallization aid before and/or during the step of crystallization of the leavening agent.

The crystallization aid is preferably added to the mother liquor from which the leavening agent is crystallized. In this case, the crystallization aid is added to the mother liquor, which is usually circulated, and in which the carbonate and optionally hydrogencarbonate and carbamate is prepared and crystallized.

The method of producing the leavening agents has long been known to the skilled person. For example, ammonium compounds such as ammonium carbonate, bicarbonate, and carbamate are prepared by reacting the corresponding amounts of ammonia, typically 10% to 20%, and carbon dioxide added in excess, typically 30% to 65%, in aqueous mother liquor, at the corresponding pressure, typically 1 to 6 bar, and temperature, typically 30 to 65° C., followed by crystallization, isolation, and drying of the precipitate.

A detailed description of the production of leavening agents is found in Ullmann's Encyclopedia of Industrial Chemistry, 2008 edition, for example.

The metered amount of the crystallization aid into the mother liquor corresponds in the case of continuous processes, after a concentration phase, to the amount of mixing component present in the isolated crystals.

Following the preparation of the mixed crystals of the invention, they may optionally be admixed with further auxiliaries; examples are known anticaking agents such as cornflour, magnesium oxide and/or magnesium carbonate, or known release agents such as salts of fatty acids, as for example steric acid, calcium stearate and/or magnesium stearate, silicates, silicon dioxide, talc or other customary anticaking agents. An advantage of the method of the invention, however, is that such additions can be greatly reduced in amount or even not used at all. Metered additions of more than 5000 ppm of magnesium carbonate are generally an advantage only for extreme storage temperatures and storage times.

The present invention further provides for the use of the mixed crystals of the invention for producing bakery products, as acid regulator in other foods, in production of cosmetics products, in the synthesis and formulation of pharmaceutical products, and also as blowing agent in industrial processes such as, for example, the production of foam rubber, or for fire-extinguishing formulations.

The present invention further provides a method of producing bakery products which comprises using the mixed crystals of the invention as modified leavening agent. The method of producing bakery products may for example be carried out continuously (automatic baking line).

The method of producing bakery products is otherwise carried out in a customary way familiar to the skilled person.

The method of producing bakery products is therefore further characterized in that a dough is prepared which typically comprises a starch source such as flour and/or potato starch, a protein source such as egg white, frequently fats such as butter, oil and/or margarine, and usually further ingredients such as sugar, spices, fruits or the like. The ingredients are subjected to intense mechanical mixing in a usual way, as for example by stirring or kneading. In addition to the leavening agent, further ingredients may be used that likewise lead to porosity in the bakery products produced, examples being yeast and/or sour dough, and the porosity can also be increased by the blowing of gases such as air into the dough. The leavening agent can optionally also be premixed with individual components of the dough prior to actual dough preparation. It may be mixed, furthermore, with dry components of the dough, examples being flour, sugar, spices, other flavors and/or dry egg, to form a baking mix, from which, by addition of liquid, a dough is prepared and is then baked.

The amount of the added leavening agent with modified crystal morphology is selected such as to bring about the desired porosity, something which is easily optimized by means of a few routine tests.

The amount of leavening agent is typically selected such that advantageously 1.5 to 3.5 g of gases (carbon dioxide, ammonia and/or steam) are developed per 100 g of the starch source used (e.g., flour and/or potato starch), preferably 2 to 3 g of gases, more particularly 2.35 to 2.85 g of gases.

The mixed crystals of the invention are added typically in an amount of 0.1% to 5% by weight, based on the total dough produced, preferably 0.5% to 2% by weight, more particularly about 1% by weight.

Where less porous bakery products are being produced, the amount should be reduced accordingly, and for more porous products it should be increased accordingly.

The advantage of the present invention is that the mixed crystals of the invention have a circular shape and smooth surfaces. In the course of storage and in the course of the application of the mixed crystals of the invention as a modified leavening agent, therefore, substantially fewer agglomerates which, furthermore, are easier to loosen again are formed—in other words, the formation of large gas bubbles in the baking process and, consequently, an inhomogeneous distribution of porosity can be prevented.

Since the crystallization aid is present with the leavening agent in a mixed crystal, it is also not possible for unwanted separation to come about, at any time.

Furthermore, the objective of preventing instances of caking is achieved with just a very small amount of crystallization aid. In addition there is no additional step necessary for the production of the leavening agent.

Bakery products with a readily controllable porosity can be produced.

EXAMPLES

1. Crystallization

Ammonium bicarbonate (ABC), water, and additive were heated to 40° C. with stirring, in accordance with table 1. Following complete dissolution, cooling took place rapidly to 0° C., with stirring. The resultant crystals were cooled, dried, and inspected under the microscope at a magnification 20:1.

TABLE 1

| | ABC [g] | Water [g] | Additive | |
|---|---|---|---|---|
| Blank test | | | | |
| 1. (comparative test) | 30.8 | 131.2 | 0 | FIG. 2 |
| | ABC [g] | Water [g] | Additive [mg] | |
| Pectin | | | | |
| 2. | 30.8 | 131.2 | 0.31 (10 ppm) | FIG. 3 A |
| 3. | 30.8 | 131.2 | 1.5 (50 ppm) | FIG. 3 B |

TABLE 1-continued

Figure 4:
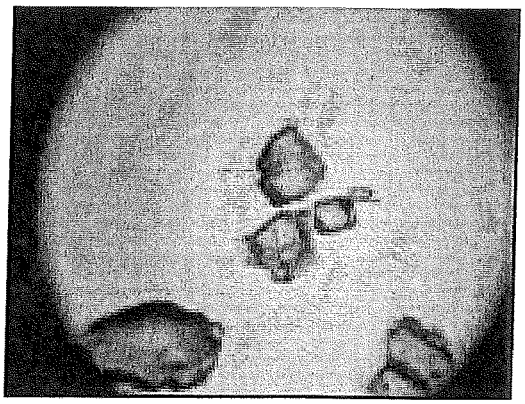
Figure 4:
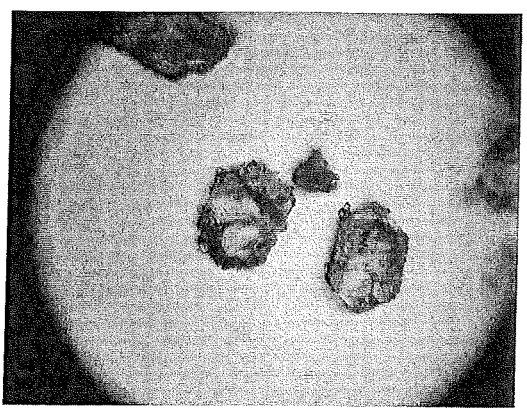
Figure 4:
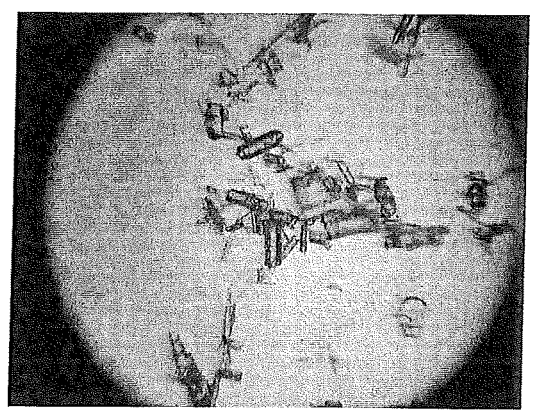
Figure 5:
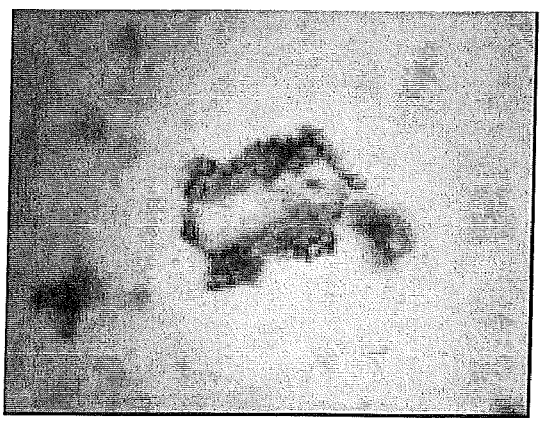

| | ABC [g] | Water [g] | Additive [mg] | |
|---|---|---|---|---|
| Tylose | | | | |
| 4. | 30.8 | 131.2 | 0.15 (5 ppm) | FIG. 4 A |
| 5. | 30.8 | 131.2 | 0.75 (25 ppm) | FIG. 4 B |
| 6. (comparative test, in analogy to EP 1 161 872) | 30.8 | 131.2 | 31 (1000 ppm) | FIG. 4 C |
| Gelatin | | | | |
| 7. | 30.8 | 131.2 | 0.31 (10 ppm) | FIG. 5 |

The results are shown in FIGS. 2 to 5.

Figure 2:
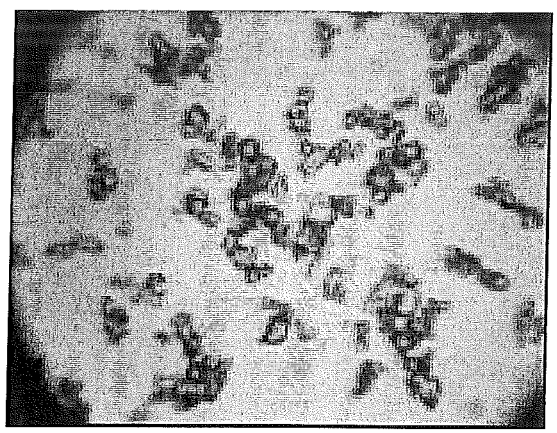
FIG. 2 illustrates the baking product according to the comparative test.

Clearly apparent from FIGS. 2 and 4C is the agglomeration tendency of the ammonium bicarbonate crystals. The mixed crystals of the invention (FIGS. 3A/B, 4 A/B, and 5), in contrast, have only individual crystals, which show no agglomeration tendency, at the same magnification.

2. Penetration Test

Sample 1: Mixed crystals of ABC and 2 ppm of pectin, 3000 ppm of magnesium carbonate as anticaking agent Sample 2: ABC without addition of crystallization aid (prior art), 3000 ppm of magnesium carbonate as anticaking agent Both samples were stored under a pressure of 1.25 kPa for 2 weeks. The penetrometer was then placed on the middle of the stored product and gradually loaded with greater weights. A proportional and deep penetration of the cone per unit weight is a reflection of a readily flowable product. The layer thickness was 15 mm. The results are shown in table 2 and in FIG. 6.

TABLE 2

| Weight of the cone [g] | Sample 1 Penetration depth [mm] | Sample 2 Penetration depth [mm] |
|---|---|---|
| 0 | 0 | 0 |
| 170 | 3 | 1 |
| 350 | 5 | 1 |
| 531 | 10 | 3 |
| 713 | 12 | 3 |
| 896 | 15 | 3 |
| 1081 | | 3 |
| 1267 | | 5 |
| 1454 | | 5 |
| 1642 | | 5 |
| 1831 | | 5 |
| 2021 | | 5 |
| 2206 | | 5 |
| 2391 | | 5 |
| 2579 | | 5 |

Whereas the cone, in the case of sample 2, penetrated the product only sporadically (plateaus in the penetration depth/weight curve) and not deeply even under a relatively high weight load, the cone in the case of sample 1 sank into the product almost proportionally with increasing weight, until the product was completely displaced.

From the results in table 2 it is evident that the mixed crystals of the invention (sample 1), in comparison to the prior art (sample 2), are very readily flowable and do not even start to exhibit instances of caking, even under pressure. The sample from the prior art (sample 2), exhibits instances of caking even under gentle pressure, however.

3. Flowability After Storage

For the storage test, 25-kg plastic bags were filled with freshly produced product and were loaded with a weight (pallets with storage product). The bags were subsequently opened and inspected. The storage conditions are summarized in tables 3.1 to 3.3.

The degree of caking of ammonium bicarbonate (ABC) was graded on a scale from 1 to 5.
Assessment:
1=ABC is lump-free and readily flowable
2=ABC is easily loosenable and then is readily flowable; no small lumps remain
3=ABC is loosenable and then flowable; small lumps remain
4=ABC is difficult to loosen and then of limited flowability; larger lumps remain
5=ABC not loosenable/not flowable All of the samples in the tables below were admixed additionally, after crystallization, with the stated amounts of magnesium carbonate as anticaking agent.

TABLE 3.1

|  | ABC as per prior art, 500 ppm of MgCO$_3$ | Mixed crystals of ABC and 2 ppm of pectin, 500 ppm of MgCO$_3$ |
| --- | --- | --- |
| Load: 1 tonne Storage: 1 month | (FIG. 7 A) | (FIG. 7 B) |
| Evaluation: | 4 | 1 |

TABLE 3.2

|  | ABC as per prior art, 3000 ppm of MgCO$_3$ | Mixed crystals of ABC and 2 ppm of pectin, 3000 ppm of MgCO$_3$ |
| --- | --- | --- |
| Load: 2 tonnes Storage: 5 months | (FIG. 8 A) | (FIG. 8 B) |
| Evaluation: | 5 | 2 |

TABLE 3.3

|  | ABC as per prior art 8000 ppm of MgCO$_3$ | Mixed crystals of ABC and 2 ppm of pectin, 8000 ppm of MgCO$_3$ |
| --- | --- | --- |
| Load: 2 tonnes Storage: 6 months | (FIG. 9 A) | (FIG. 9 B) |
| Evaluation: | 4 | 1 |

FIG. 7: whereas the prior-art ABC has undergone severe caking, and relatively large lumps remain even when the powder is moved (loosening attempts), the mixed crystals of the invention, with pectin, are very readily flowable and absolutely lump-free.

FIG. 8: whereas the prior-art ABC has undergone very severe caking, and large, solid lumps remain even when the bag is knocked, the mixed crystals of the invention, with pectin, are readily flowable. The small lumps disappear when the product is moved.

Figure 9:
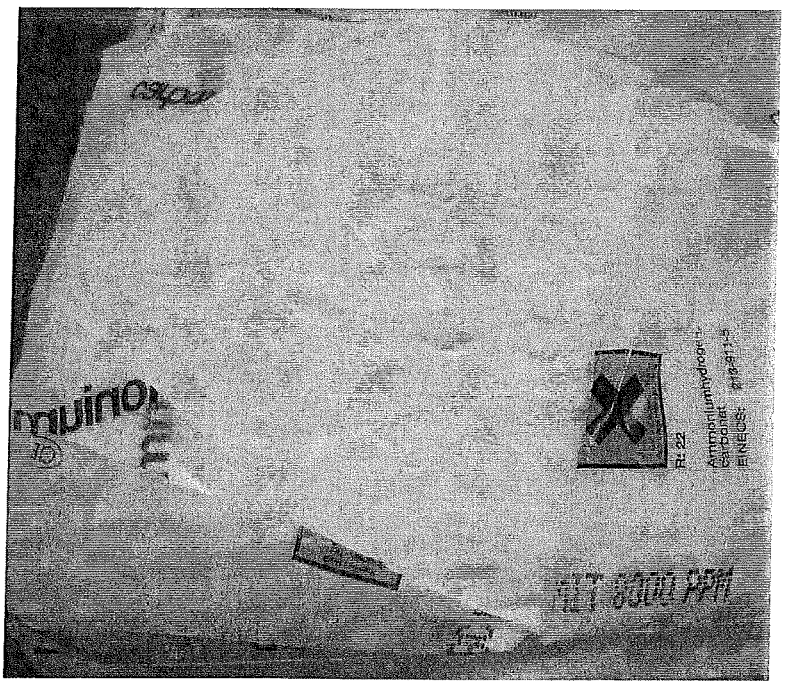
Figure 9:
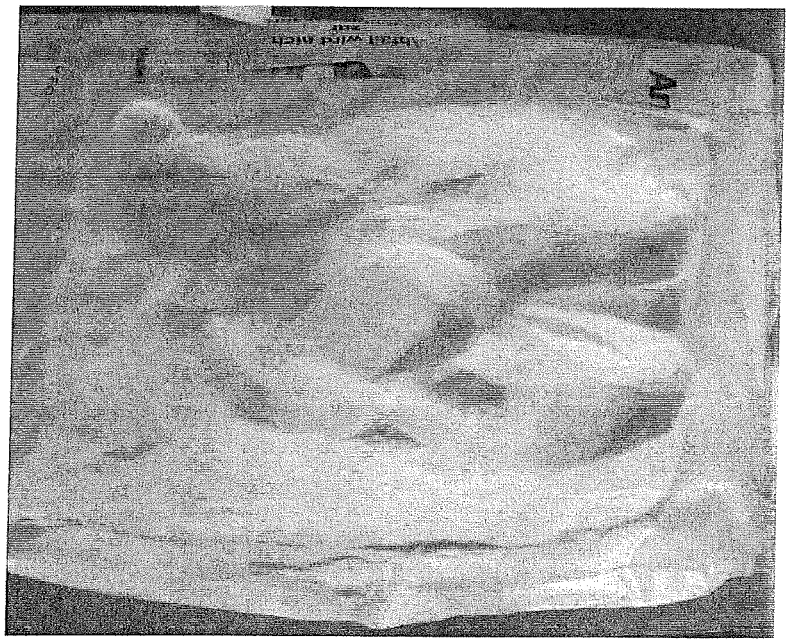

FIG. 9: whereas the prior-art ABC has undergone severe caking, the mixed crystals with pectin are readily flowable, without the formation of lumps.

4. Flowability After Storage in Comparison to EP 1 161 872 (as Mixed Crystal)

An approximately 5 mm thick layer of ABC mixed crystals with 25 ppm and 1000 ppm of Tylose with a diameter of about 6 cm was stored for 10 minutes under a weight of 13.75 kg (approximately 500 g/cm$^2$ pressure). Thereafter the compacted product was transferred to a further piece of paper, by lifting of the paper, and the degree of caking was assessed on the basis of the scale from example 3.

TABLE 4

|  | ABC with 1000 ppm of Tylose (comparative example in analogy to EP 1 161 872) | ABC with 25 ppm of Tylose |
| --- | --- | --- |
| 10 Minutes at 500 g/cm$^2$ pressure | (FIG. 10 A) | (FIG. 10 B) |
| Result: | 3 | 1 |

The ABC mixed crystals with 1000 ppm of Tylose are indeed loosenable and then flowable, but lumps remain which in the baking process can lead to undesirably large gas bubbles and, consequently, to unwanted inhomogeneous pore distribution.

5. Flowability After Storage in Comparison to EP 1 161 872 (as Tylose-Coated ABC Pure Crystal)

For the storage test, 25-kg plastic bags were filled with freshly produced product and were loaded with weight (pallets with storage product). The bags were then opened and inspected. Comparison was made between ABC coated with 1000 ppm by weight of Tylose, and mixed crystals of ABC and 25 ppm by weight of Tylose. The flowability was evaluated on the basis of the evaluation scale set out in section 3 of the examples.

TABLE 5

|  | ABC coated with 1000 ppm by weight of Tylose, 500 ppm by weight of MgCO$_3$ | Mixed crystals of ABC and 25 ppm by weight of Tylose, 500 ppm by weight of MgCO$_3$ |
| --- | --- | --- |
| Evaluation (no storage) | 1 | 1 |
| Evaluation (loading: 2 tonnes, 3 days' storage) | 5 | 1 |
| Evaluation (loading: 2 tonnes, 7 days' storage) | 5 | 1 |

The ABC coated with 1000 ppm by weight of Tylose is no longer loosenable, and also not flowable, after storage with conventional loading, as in the course of transport, for example.

Note: the unit "ppm" in the examples stands for ppm by weight.

The invention claimed is:
1. Mixed crystals comprising
   a) a leavening agent comprising at least one carbonate and optionally one or more carbamates, and
   b) 0.1 to 1000 ppm by weight of a crystallization aid, based on the total amount of the leavening agent, in the form of at least one polymer, wherein the crystallization aid is selected from the group consisting of pectin E440, amidated pectin E440, and mixtures thereof, and wherein components a) and b) are present during crystallization of the mixed crystals.
2. The mixed crystals according to claim 1, wherein the at least one polymer comprises at least one hydrophilic crystallization-influencing polymer, and wherein the mixed crystals exhibit a smooth and regular structure under the influence of the at least one hydrophilic crystallization-influencing polymer.
3. The mixed crystals according to claim 1, wherein component b) is 0.5 to 1000 ppm by weight of the crystallization aid in the form of at least one polymer.

4. The mixed crystals according to claim 1, wherein component b) is 1 to 100 ppm by weight of the crystallization aid in the form of at least one polymer.

5. The mixed crystals according to claim 1, wherein the leavening agent comprises sodium carbonate, sodium hydrogencarbonate, potassium carbonate, potassium hydrogencarbonate, ammonium carbonate or ammonium hydrogencarbonate or a mixture thereof.

6. The mixed crystals according to claim 1, wherein the leavening agent comprises ammonium hydrogencarbonate.

7. A method of producing the mixed crystals according to claim 1, which comprises preparing a mother liquor of the leavening agent and crystallizing the leavening agent from the mother liquor by adding the crystallization aid before and/or during the step of crystallization of the leavening agent.

8. A method of producing bakery products, which comprises preparing a dough by mixing ingredients for the dough and the mixed crystals according to claim 1 as a modified leavening agent, or by premixing the mixed crystals according to claim 1 as a modified leavening agent with individual components of the dough prior to actual dough preparation.

9. The method of producing bakery products according to claim 8, wherein the method is carried out continuously.

10. A blowing agent in industrial processes which comprises the mixed crystals according to claim 1.

11. A material comprising the mixed crystals according to claim 1, wherein the material is a baked product, a cosmetics product or a pharmaceutical product.

12. The mixed crystals of claim 1, wherein the mixed crystals have a surface with a round shape, wherein the mixed crystals do not intermesh with one another and wherein the mixed crystals do not undergo caking.

13. The mixed crystals of claim 1, wherein the crystallization aid is in an amount from 1 to 50 ppm by weight based on the total amount of the leavening agent.

14. The mixed crystals of claim 1, wherein the at least one carbonate is selected from the group consisting of alkali metal carbonates and hydrogencarbonates.

15. The mixed crystals of claim 13, wherein the mixed crystals have a surface with a round shape, wherein the mixed crystals do not intermesh with one another and wherein the mixed crystals do not undergo caking.

* * * * *